(12) United States Patent
Fojtik

(10) Patent No.: US 10,207,057 B2
(45) Date of Patent: Feb. 19, 2019

(54) SYRINGE WITH ROTATABLE ELEMENT, SYSTEMS INCLUDING THE SYRINGE, AND ASSOCIATED METHODS

(71) Applicant: Control Medical Technology, LLC, Park City, UT (US)

(72) Inventor: Shawn P. Fojtik, Park City, UT (US)

(73) Assignee: Control Medical Technology, LLC, Park City, UT (US)

( * ) Notice: Subject to any disclaimer, the term of this patent is extended or adjusted under 35 U.S.C. 154(b) by 835 days.

(21) Appl. No.: 14/218,478

(22) Filed: Mar. 18, 2014

(65) Prior Publication Data

US 2014/0200483 A1    Jul. 17, 2014

Related U.S. Application Data

(63) Continuation of application No. 12/766,791, filed on Apr. 23, 2010, now Pat. No. 8,672,893, which is a
(Continued)

(51) Int. Cl.
*A61M 5/315*    (2006.01)
*A61M 5/31*    (2006.01)
*A61B 10/02*    (2006.01)

(52) U.S. Cl.
CPC ..... *A61M 5/31511* (2013.01); *A61B 10/0283* (2013.01); *A61M 5/3129* (2013.01); *A61M 5/3135* (2013.01); *A61M 2005/3139* (2013.01)

(58) Field of Classification Search
CPC ...... A61M 5/24; A61M 5/28; A61M 5/31511; A61M 5/31553; A61M 5/31555; A61B 10/0283; A61C 9/0026
See application file for complete search history.

(56) References Cited

U.S. PATENT DOCUMENTS

| 530,187 A | 12/1894 | Laskey |
| 870,573 A | 11/1907 | Myers |
| (Continued) | | |

FOREIGN PATENT DOCUMENTS

| DE | 196 47 529 A1 | 5/1998 |
| DE | 197 32 332 A1 | 2/1999 |
| (Continued) | | |

OTHER PUBLICATIONS

United States Patent and Trademark Office as the International Searching Authority, "International Search Report and Written Opinion" issued in related International Application No. PCT/US2008/061345, dated Sep. 16, 2008.
(Continued)

*Primary Examiner* — Theodore Stigell
*Assistant Examiner* — Matthew A Engel
(74) *Attorney, Agent, or Firm* — Durham Jones & Pinegar, P.C., Intellectual Property Law Group

(57) ABSTRACT

A syringe includes a barrel and a rotatable element on the barrel, for example, at a proximal location along the length of the barrel. The rotatable element rotates at least partially around the barrel. When a handle is associated with the rotatable element, the barrel may rotate as the handle is held substantially stationary or the handle may be rotated while the barrel and any peripheral device secured thereto remain substantially stationary. When handles are associated with a rotatable element that may be removed from a barrel, a barrel that is disassembled from the rotatable element may be replaced with another barrel of the same or a different configuration. The barrel and plunger may be configured to cause the barrel to rotate as the plunger moves along the length of the barrel. Methods of using a syringe with a rotatable element on a barrel thereof are also disclosed.

7 Claims, 5 Drawing Sheets

Related U.S. Application Data continuation-in-part of application No. PCT/US2008/061345, filed on Apr. 23, 2008, and a continuation-in-part of application No. 11/877,564, filed on Oct. 23, 2007, now Pat. No. 10,058,656.

(60) Provisional application No. 60/853,817, filed on Oct. 24, 2006.

(56) References Cited

U.S. PATENT DOCUMENTS

| | | | |
|---|---|---|---|
| 901,567 A | 10/1908 | Utschig | |
| 1,019,207 A | 3/1912 | Ward | |
| 1,218,513 A | 3/1917 | Biron | |
| 1,718,596 A * | 6/1929 | Smith | A61M 5/24 222/391 |
| 1,893,488 A | 1/1933 | Alexander | |
| 2,687,725 A | 8/1954 | Hein, Jr. | |
| 2,748,767 A * | 6/1956 | Wright | A61C 9/0026 604/209 |
| 2,904,043 A | 9/1959 | Friedman | |
| 3,016,897 A | 1/1962 | Kendrick | |
| 3,110,310 A * | 11/1963 | Cislak | A61M 5/31581 604/209 |
| 3,150,801 A | 9/1964 | Hamilton | |
| 3,212,685 A * | 10/1965 | Swan | A61M 3/00 222/386 |
| 3,281,023 A | 10/1966 | Bruck et al. | |
| 3,770,169 A | 11/1973 | Roach | |
| 3,815,785 A * | 6/1974 | Gilmont | A61M 3/00 222/46 |
| 3,840,007 A * | 10/1974 | Fish | A61M 5/315 604/117 |
| 4,020,838 A | 5/1977 | Phillips et al. | |
| 4,065,034 A * | 12/1977 | Callan | B05C 3/132 219/230 |
| 4,173,225 A * | 11/1979 | Newman | A61M 5/31555 604/210 |
| 4,187,849 A * | 2/1980 | Stim | A61M 1/008 604/236 |
| 4,198,756 A * | 4/1980 | Dragan | B05C 17/00593 222/326 |
| 4,198,975 A * | 4/1980 | Haller | A61M 5/20 604/157 |
| 4,204,539 A | 5/1980 | Van Brugge | |
| 4,330,070 A | 5/1982 | Doubleday | |
| 4,368,731 A * | 1/1983 | Schramm | A61M 5/31595 604/231 |
| 4,425,121 A | 1/1984 | Young et al. | |
| RE32,214 E * | 7/1986 | Schramm | A61M 5/31595 604/232 |
| 4,712,545 A | 12/1987 | Honkanen | |
| 4,738,664 A | 4/1988 | Prindle | |
| 4,744,789 A | 5/1988 | Johnson | |
| 4,808,165 A | 2/1989 | Carr | |
| 4,832,692 A | 5/1989 | Box et al. | |
| 4,861,339 A | 8/1989 | Jonischkeit | |
| 4,917,679 A | 4/1990 | Kronner | |
| 4,923,096 A | 5/1990 | Ennis, III | |
| 4,968,303 A * | 11/1990 | Clarke | A61M 5/24 604/187 |
| 4,994,065 A | 2/1991 | Gibbs et al. | |
| 5,027,605 A | 7/1991 | Hardesty | |
| 5,037,399 A | 8/1991 | Reichert et al. | |
| 5,045,066 A | 9/1991 | Scheuble et al. | |
| 5,069,421 A | 12/1991 | Kishi et al. | |
| 5,078,690 A | 1/1992 | Ryan | |
| 5,112,307 A | 5/1992 | Haber et al. | |
| 5,133,483 A | 7/1992 | Buckles | |
| 5,135,507 A | 8/1992 | Haber et al. | |
| 5,139,488 A | 8/1992 | Klein | |
| 5,150,488 A | 9/1992 | Yuan et al. | |
| 5,176,647 A | 1/1993 | Knoepfler | |
| 5,188,610 A | 2/1993 | Rains | |
| 5,209,732 A | 5/1993 | Lampropoulos et al. | |
| 5,213,115 A * | 5/1993 | Zytkovicz | A61M 5/488 128/898 |
| 5,228,883 A * | 7/1993 | Blakely | A61M 5/24 222/327 |
| 5,279,563 A * | 1/1994 | Brucker | A61M 25/10184 604/100.03 |
| 5,288,285 A | 2/1994 | Carter | |
| 5,304,147 A | 4/1994 | Johnson et al. | |
| 5,306,147 A | 4/1994 | Dragan et al. | |
| 5,308,358 A | 5/1994 | Bond et al. | |
| 5,336,201 A | 8/1994 | von der Decken | |
| 5,350,365 A | 9/1994 | De Godoy Moreira | |
| 5,368,202 A | 11/1994 | Smrt | |
| 5,425,743 A * | 6/1995 | Nicholas | A61B 17/2909 606/151 |
| 5,453,093 A | 9/1995 | Haining | |
| 5,480,409 A | 1/1996 | Riza | |
| 5,499,998 A | 3/1996 | Meade | |
| 5,505,704 A | 4/1996 | Pawelka et al. | |
| 5,507,727 A | 4/1996 | Crainich | |
| 5,507,730 A | 4/1996 | Haber et al. | |
| 5,511,556 A * | 4/1996 | DeSantis | A61B 10/0283 600/562 |
| 5,531,708 A | 7/1996 | Woodruff | |
| 5,560,373 A | 10/1996 | De Santis | |
| 5,562,655 A | 10/1996 | Mittelstadt et al. | |
| 5,591,135 A | 1/1997 | Sullivan | |
| 5,591,176 A | 1/1997 | Henderson et al. | |
| 5,645,561 A | 7/1997 | Smith et al. | |
| 5,685,862 A | 11/1997 | Mahurkar | |
| 5,692,642 A | 12/1997 | Brattesani | |
| 5,722,829 A | 3/1998 | Wilcox et al. | |
| 5,733,258 A * | 3/1998 | Lane | A61M 5/31581 604/209 |
| 5,733,259 A | 3/1998 | Valcke et al. | |
| 5,735,874 A | 4/1998 | Measamer et al. | |
| 5,743,436 A * | 4/1998 | Wilcox | A61C 9/0026 222/137 |
| 5,749,968 A | 5/1998 | Melanson et al. | |
| 5,755,362 A | 5/1998 | Rodriguez, Jr. et al. | |
| 5,807,340 A | 9/1998 | Pokras | |
| 5,830,194 A | 11/1998 | Anwar et al. | |
| 5,851,214 A | 12/1998 | Larsen et al. | |
| 5,867,911 A | 2/1999 | Yates et al. | |
| 5,881,928 A | 3/1999 | Register et al. | |
| 5,893,488 A | 4/1999 | Hoag et al. | |
| 5,951,517 A | 9/1999 | Lampropoulos et al. | |
| 5,961,494 A | 10/1999 | Hogan | |
| 5,961,496 A | 10/1999 | Nielsen et al. | |
| 5,964,380 A | 10/1999 | Hazzard et al. | |
| 5,964,736 A * | 10/1999 | Lane | A61M 5/31581 604/207 |
| 5,992,694 A | 11/1999 | Keller | |
| 6,007,515 A | 12/1999 | Epstein et al. | |
| 6,024,728 A | 2/2000 | Schulz | |
| 6,030,368 A | 2/2000 | Anwar et al. | |
| 6,047,861 A | 4/2000 | Vidal et al. | |
| 6,080,136 A | 6/2000 | Trull et al. | |
| 6,117,158 A | 9/2000 | Measamer et al. | |
| 6,183,444 B1 | 2/2001 | Glines et al. | |
| 6,213,984 B1 | 4/2001 | Lane et al. | |
| 6,241,708 B1 | 6/2001 | Reilly et al. | |
| 6,264,637 B1 | 7/2001 | Hogan | |
| 6,280,401 B1 | 8/2001 | Mahurkar | |
| 6,368,307 B1 | 4/2002 | Ziemba et al. | |
| 6,406,460 B1 | 6/2002 | Hogan | |
| 6,439,439 B1 | 8/2002 | Rickard et al. | |
| 6,585,696 B2 | 7/2003 | Petersen et al. | |
| 6,607,512 B2 | 8/2003 | Oliver et al. | |
| 6,752,781 B2 | 6/2004 | Landau et al. | |
| 6,764,466 B1 | 7/2004 | Staats et al. | |
| 6,802,824 B2 | 10/2004 | Mickley et al. | |
| 7,041,084 B2 | 5/2006 | Fojtik | |
| 7,097,636 B2 | 8/2006 | Pessin | |
| 7,125,395 B2 | 10/2006 | Hommann et al. | |
| 7,534,234 B2 * | 5/2009 | Fojtik | A61B 5/153 222/386 |

(56) References Cited

U.S. PATENT DOCUMENTS

| | | | |
|---|---|---|---|
| 7,674,247 B2 | 3/2010 | Fojtik | |
| 7,988,677 B2* | 8/2011 | Fojtik | A61M 5/007 222/470 |
| 8,021,333 B2* | 9/2011 | Kaal | A61M 5/3234 604/110 |
| 8,672,893 B2* | 3/2014 | Fojtik | A61M 5/3129 600/562 |
| 2002/0022805 A1 | 2/2002 | Lane | |
| 2002/0183698 A1 | 12/2002 | Quinn et al. | |
| 2003/0078912 A1 | 4/2003 | Oliver et al. | |
| 2003/0139706 A1* | 7/2003 | Gray | A61M 5/3135 604/199 |
| 2003/0187400 A1* | 10/2003 | Liao | A61M 5/3234 604/195 |
| 2004/0116873 A1* | 6/2004 | Fojtik | A61M 5/007 604/221 |
| 2004/0116893 A1 | 6/2004 | Spohn et al. | |
| 2004/0164097 A1 | 8/2004 | Orecchia et al. | |
| 2004/0166873 A1 | 8/2004 | Simic et al. | |
| 2004/0210200 A1 | 10/2004 | Gerondale et al. | |
| 2005/0070848 A1 | 3/2005 | Kim et al. | |
| 2005/0070912 A1 | 3/2005 | Voellmicke | |
| 2005/0137575 A1 | 6/2005 | Thompson et al. | |
| 2006/0247578 A1 | 11/2006 | Arguedas et al. | |
| 2007/0010788 A1 | 1/2007 | Evans | |
| 2007/0265573 A1 | 11/2007 | Fojtik | |
| 2008/0004703 A1* | 1/2008 | Trieu | A61F 2/30756 623/17.16 |
| 2010/0217122 A1* | 8/2010 | Fumiyama | A61M 5/3129 600/432 |
| 2011/0065992 A1 | 3/2011 | Bissinger | |
| 2014/0200483 A1* | 7/2014 | Fojtik | A61M 5/3129 600/566 |

FOREIGN PATENT DOCUMENTS

| | | |
|---|---|---|
| EP | 0 474 218 A1 | 3/1992 |
| EP | 0 565 045 A1 | 10/1993 |
| EP | 0 919 251 A2 | 6/1999 |
| EP | 1 066 797 A1 | 1/2001 |
| EP | 1 440 706 A1 | 7/2004 |
| EP | 1 148 834 B1 | 4/2007 |
| EP | 1 301 227 B1 | 11/2007 |
| FR | 2 009 514 A | 2/1970 |
| FR | 2.207.728 | 6/1974 |
| FR | 2 207 728 A | 6/1974 |
| FR | 2 362 638 | 3/1978 |
| FR | 2 683 140 A | 5/1993 |
| GB | 1 456 650 | 11/1976 |
| JP | 08-039471 | 2/1996 |
| JP | 2004-527333 | 9/2004 |
| WO | 99/08735 A2 | 2/1999 |
| WO | 00/44300 A1 | 8/2000 |
| WO | 02/07812 A2 | 1/2002 |
| WO | 02/094343 A2 | 11/2002 |
| WO | 20041062713 A1 | 7/2004 |
| WO | 2007/133615 A2 | 11/2007 |

OTHER PUBLICATIONS

European Patent Office as the International Searching Authority, "International Search Report and Written Opinion" issued in related International Application No. PCT/US2008/061239, dated Jul. 30, 2008.

European Patent Office, "Supplementary European Search Report," dated Jan. 15, 2015, in European patent application No. EP08780563.6.

Written Opinion of the International Searching Authority in International Application No. PCT/US2008/061239 dated Apr. 23, 2010.

Japanese Patent Office, "Notice of Reason for Rejection" dated Mar. 30, 2015, in Japanese patent application No. 2014-147359.

Japanese Patent Office, "Office Action" dated May 7, 2014, in Japanese patent application No. 2010-531083.

* cited by examiner

SYRINGE WITH ROTATABLE ELEMENT, SYSTEMS INCLUDING THE SYRINGE, AND ASSOCIATED METHODS

CROSS-REFERENCE TO RELATED APPLICATIONS

This application is a continuation of U.S. patent application Ser. No. 12/766,791, filed on Apr. 23, 2010, and titled SYRINGE WITH ROTATABLE ELEMENT, ASPIRATION SYSTEMS INCLUDING THE SYRINGE, AND ASSOCIATED METHODS (hereinafter "the '791 Application"). The '791 Application was a continuation-in-part of PCT International Patent Application PCT/US2008/061345, filed on Apr. 23, 2008, and titled SYRINGE WITH ROTATABLE ELEMENT, ASPIRATION SYSTEMS INCLUDING THE SYRINGE, AND ASSOCIATED METHODS (hereinafter "the '345 International Application"). The '791 Application was a continuation-in-part of U.S. patent application Ser. No. 11/877,564, filed on Oct. 23, 2007, and titled SYRINGE WITH ROTATABLE ELEMENT, INFUSION/ASPIRATION SYSTEMS INCLUDING THE SYRINGE, AND ASSOCIATED METHODS (hereinafter "the '564 Application"). The '564 Application claimed the benefit of the filing date of U.S. Provisional Patent Application No. 60/853,817, filed on Oct. 24, 2006, titled LOCKABLE, ADJUSTABLE HINGE MECHANISMS FOR SYRINGES (hereinafter "the '817 Provisional Application"). The entire disclosures of the '791 Application, the '345 International Application, the '564 Application and the '817 Provisional Application are hereby incorporated in their entireties, by this reference.

TECHNICAL FIELD

The present invention relates generally to syringes and, more specifically, to syringes with circumferentially rotatable elements on the barrels thereof. The present invention also relates to systems that include aspiration syringes with rotatable elements, as well as to methods for using the syringes of such systems.

SUMMARY

In one aspect, the present invention includes syringes with rotatable elements, or "slip rings." An embodiment of such a syringe includes a syringe barrel with a ring or other rotatable element concentrically disposed about a section of the barrel. As an example, the rotatable element may be disposed at or near a proximal end of the barrel (i.e., the end into which a plunger is introduced). The rotatable element is configured to rotate relative to the barrel. In some embodiments, at least a portion of the rotatable element is captured within a groove that extends around a section of the barrel (e.g., circumferentially, etc.). In other embodiments, one or more features that protrude (e.g., a thread, a lip, a series of aligned protrusions, etc.) from the barrel of the syringe (e.g., in a circumferential arrangement, etc.) engage a groove formed in an inner surface of the rotatable element.

According to another aspect of the present invention, a syringe barrel with a slip ring may be used as part of a more complex syringe, such as an aspiration syringe (e.g., a syringe with handles that are leveraged or otherwise provide a mechanical advantage). In such a syringe, the rotatable element may be secured to a handle, which is typically held during use of the syringe, while the barrel of the syringe is free to rotate relative to the orientation in which the handle is held.

In a further aspect, an aspiration system of the present invention may include a syringe with a rotatable element, aspiration handles, and an aspiration element, such as a catheter, needle, or the like, secured to a distal end of the barrel. In use, the barrel may rotate relative to a handle that has been secured thereto (e.g., in coupling the barrel to a peripheral device, such as a catheter or needle), or the handle may rotate relative to the barrel (e.g., in use of the syringe while the barrel is coupled to a peripheral device). Such a feature eliminates the need for costly rotatable connections between the syringe barrel and the aspiration element.

While some embodiments of such a syringe include conventionally configured barrels and plungers, other embodiments of a syringe according to the present invention include barrels that are configured to rotate as their corresponding plungers are drawn through the barrels. Embodiments that include such rotating syringes may be used in a variety of procedures, including, but not limited to, biopsy or coring techniques, to rotate catheters to dislodge obstructions and/or mix fluids prior to or during sample aspiration, and the like.

In each of the foregoing embodiments, the barrel of the syringe and, optionally, an aspiration element that has been coupled to the barrel may rotate freely relative to gripping elements or handles, which may protrude from or be secured to the rotatable element. Thus, the barrel may remain stationary or substantially stationary as the gripping elements or handles are moved rotationally relative to an axis of the barrel, or the gripping elements or handles may remain stationary or substantially stationary as the barrel is rotated.

Other features and advantages of the present invention will become apparent to those of ordinary skill in the art through consideration of the ensuing description, the accompanying drawings, and the appended claims.

BRIEF DESCRIPTION OF THE DRAWINGS

In the drawings, which depict features of various aspects of the present invention.

DETAILED DESCRIPTION

Figure 1:
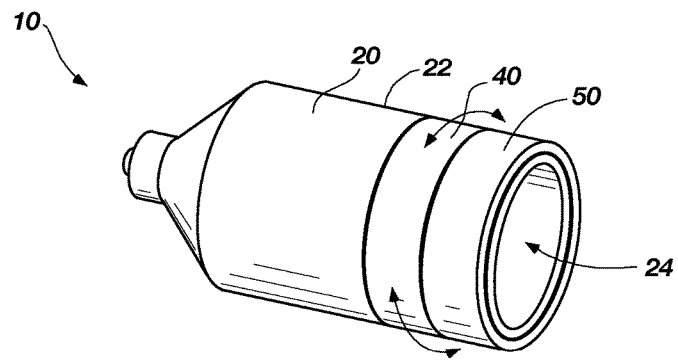
FIG. 1 is a perspective view of an embodiment of a syringe according to the present invention, which includes a rotatable element around a portion of a syringe barrel.
Figure 2:
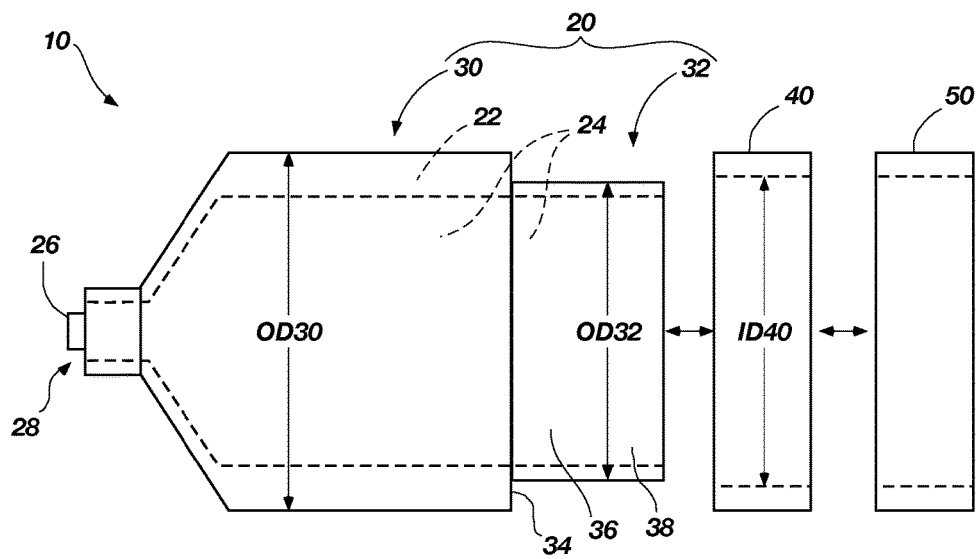
FIG. 2 is a side assembly view of the embodiment of the syringe shown in FIG. 1.
Figure 3:
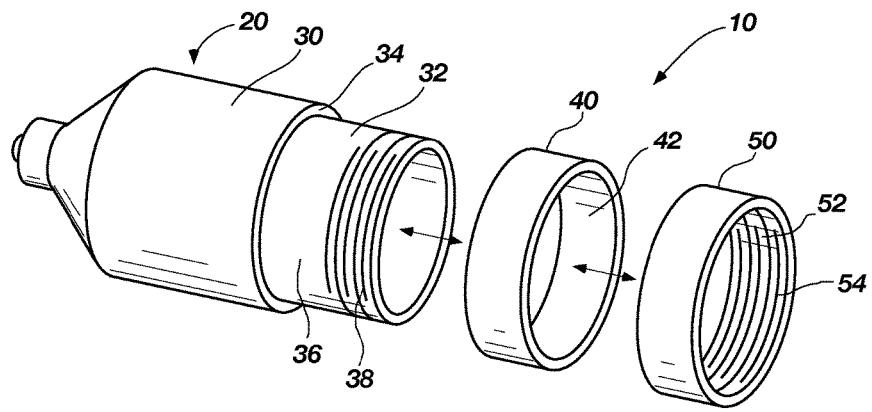
FIG. 3 is a perspective assembly view of the embodiment of the syringe shown in FIG. 1.

With reference to FIGS. 1 through 3, an embodiment of syringe 10 with a barrel 20 and a rotatable element 40 that spins about a circumference of barrel 20 is depicted. Barrel 20 includes an outer wall 22 that defines a receptacle 24 that extends axially through barrel 20.

A main body 30 of barrel 20, including a central portion of barrel 20, has a substantially uniform outer diameter OD30. At its distal tip 26, outer wall 22 tapers to a much smaller outer diameter, which may form a standard coupling element 28, which may be coupled to an aspiration needle (e.g., a hypodermic needle, biopsy needle, etc.), a catheter, or the like. A proximal end 32 of barrel 20 may also have a substantially uniform outer diameter OD32 but, as shown, its outer diameter OD32 may be smaller than outer diameter OD30 of main body 30, such that a proximal ridge 34 is defined at a boundary between main body 30 and proximal end 32.

In the illustrated embodiment, proximal end 32 includes a distally located axle 36, which may have a substantially smooth surface, and a proximally located retention feature 38. As shown, retention feature 38 may comprise threads or other, similar engagement features that are configured to receive, engage, and retain a separate locking element 50, an example of which is provided in further detail below.

Rotatable element 40, which may be annular in shape (i.e., ring-shaped), has a substantially constant inner diameter ID40 that is slightly larger than the outer diameter OD32 of proximal end 32 of barrel 20 but smaller than the outer diameter OD30 of main body 30 of barrel 20, allowing rotatable element 40 to be concentrically placed on proximal end 32. More specifically, rotatable element 40 may be placed over axle 36, adjacent to proximal ridge 34. An inner surface 42 of rotatable element 40 may be substantially smooth. Smoothness of one or both of inner surface 42 and axle 36 may facilitate the free rotation of rotatable element 40 at least partially around axle 36.

As noted, syringe 10 may also include a locking element 50. Locking element 50 may have an inner surface 52 with an engagement feature 54 (e.g., the illustrated threads, etc.) that cooperates with a complementary engagement feature of retention feature 38 at proximal end 32 of barrel 20. When locking element 50 is disposed on retention feature 38, an outer surface of axle 36 is circumferentially recessed relative to outer surfaces of main body 30 of barrel 20 and locking element 50; i.e., a circumferential groove 56 (see FIG. 7) is formed between main body 30 and locking element 50. The dimensions (e.g., a depth) of the resulting circumferential groove 56 axially retain rotatable element 40 over axle 36.

Figure 4:
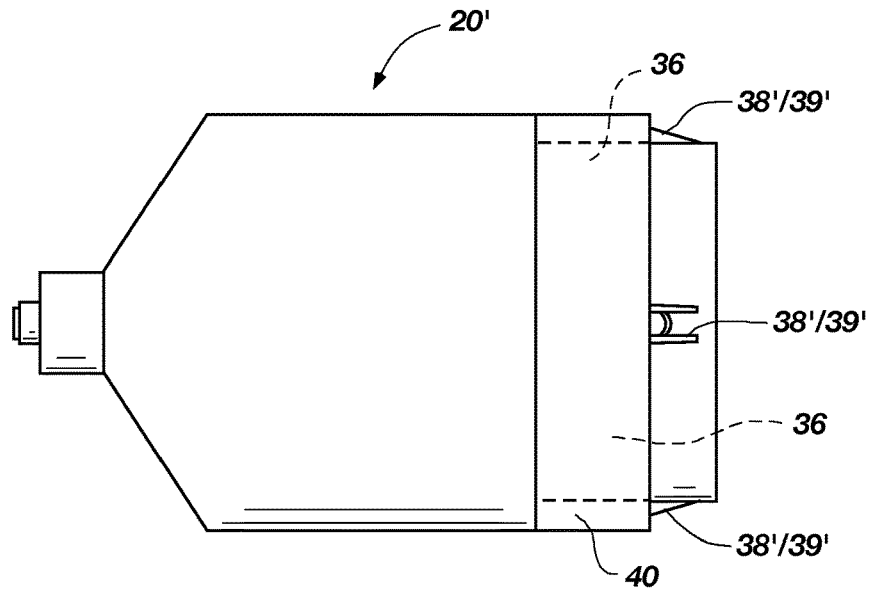
FIG. 4 is a side assembly view of another embodiment of a syringe that incorporates teachings of the present invention.

As an alternative to embodiments that include locking elements 50 that are configured for assembly with a retention feature 38 of a barrel 20 of a syringe 10, another embodiment of barrel 20' may include a retention feature 38', as shown in FIG. 4, which may facilitate the assembly of a rotatable element 40 with barrel 20', but prevent its removal from barrel 20'. For example, retention feature 38' may include one or more tabs 39' configured and oriented to facilitate the placement of rotatable element 40 over axle 36, but prevent rotatable element 40 from being removed from axle 36'. In a more specific embodiment, tabs 39' may be oriented and configured to protrude somewhat from an outer surface of the remainder of retention feature 38'. When rotatable element 40 is positioned on retention feature 38' and slid distally toward axle 36', tabs 39' may be pressed radially inward, allowing rotatable element 40 to slide thereover and onto axle 36'. Once rotatable element 40 has been positioned properly upon axle 36', tabs 39' resiliently rebound to their relaxed state, in which they protrude radially from the surface of the remainder of retention feature 38' and retain rotatable element 40 in place on axle 36'.

Figure 5:
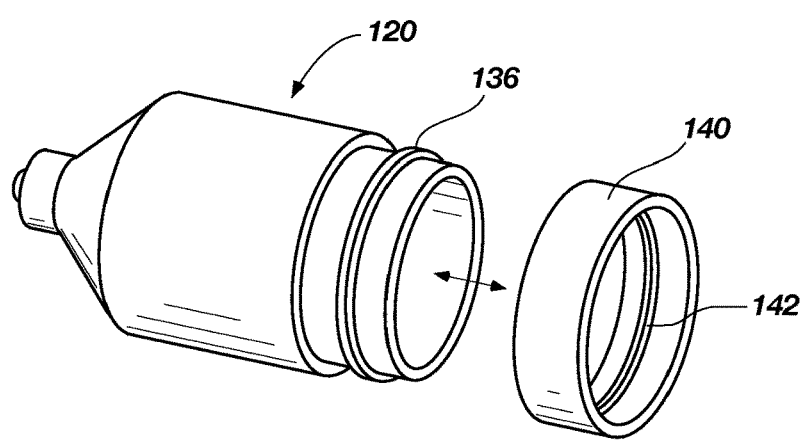
FIG. 5 is a perspective assembly view of an embodiment of a syringe with a circumferentially protruding guide for retaining a rotatable element.

FIG. 5 shows another embodiment of barrel 120, which includes one or more protrusions 136 (e.g., a single fillet or ridge, a plurality of aligned protrusions, etc.) that extend circumferentially about a portion of barrel 120. A rotatable element 140 that is configured for assembly with barrel 120 may have a somewhat annular shape and include a groove 142 for receiving protrusion(s) 136. Groove 142 and protrusion(s) 136 are configured to enable rotatable element 140 to rotate at least partially around barrel 120. Protrusion(s) 136 may be configured to facilitate the assembly of rotatable element 140 with barrel 120 while preventing the disassembly of rotatable element 140 from barrel 120. Alternatively, rotatable element 140 may be configured (e.g., with appropriate positioned slots, a hinge and locking element, etc.) to facilitate its placement over and retention by protrusion(s) 136.

Figure 6:
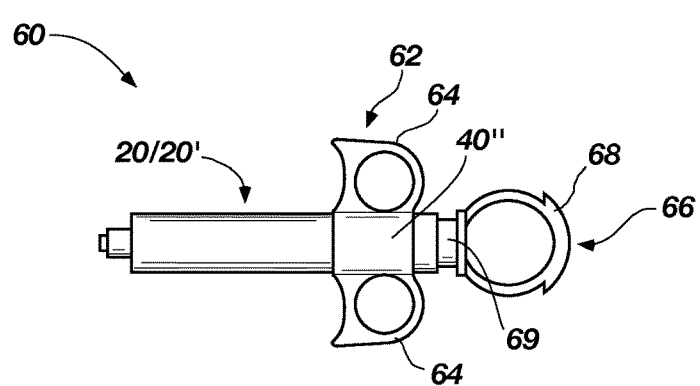
FIG. 6 is a perspective view of an embodiment of a syringe barrel with control syringe finger rings on a rotatable element.

Turning now to FIG. 6, an embodiment of a control syringe 60 according to the present invention includes a barrel 20, 20' and a rotatable element 40" with gripping elements 64, such as finger loops or other elements that are configured to be held by a user's fingers that protrude therefrom to form a handle 62. Barrel 20, 20' is particularly useful with a plunger 66 that includes a thumb loop 68 at its proximal end 69.

Figure 7:
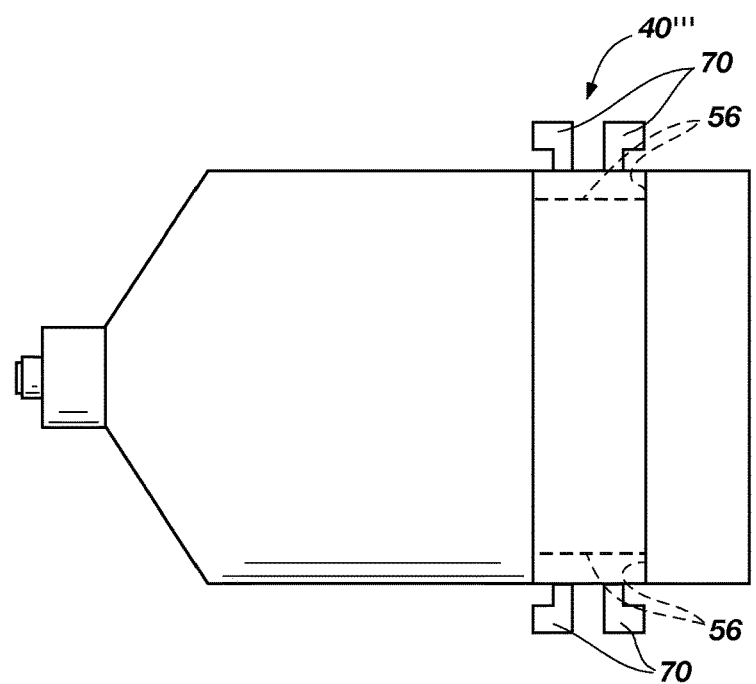
FIG. 7 is a top view of an embodiment of a syringe barrel with hinge elements protruding from a rotatable element.

Another variation of rotatable element 40''' is shown in FIG. 7. Rotatable element 40''' includes means for coupling to a handle, such as the depicted hinge elements 70. As depicted, hinge elements 70 may protrude from opposite sides of rotatable element 40'''. The axis of rotation of hinge elements 70 may intersect a central axis through rotatable element 40'''. With such an arrangement, when rotatable element 40''' is in place over an axle 36 (FIGS. 1 through 4) of a syringe barrel 20, 20', the central axis through rotatable element 40''' will substantially align with a central axis through the length of barrel 20, 20'. Thus, in such an arrangement, the axis of rotation of hinge elements 70 will also intersect the central axis through barrel 20, 20'.

Figure 8:
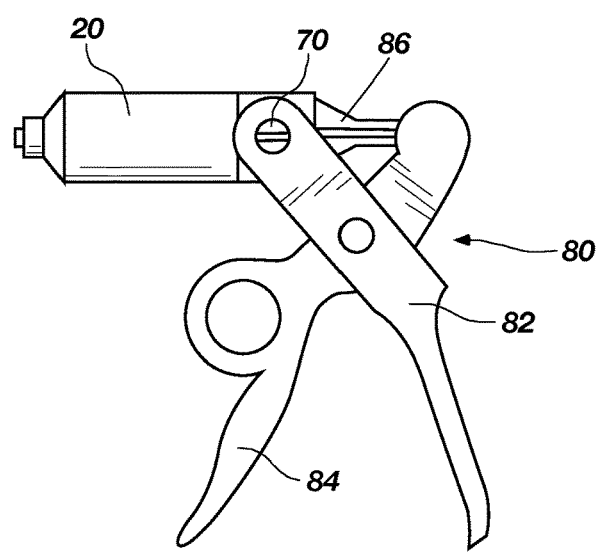
FIG. 8 is a side view of a syringe with a member of pliers-grip handles coupled to the hinge elements shown in FIG. 7.

Hinge elements 70 of the variation of rotatable element 40''' shown in FIG. 7 may facilitate pivotal assembly of rotatable element 40''' with a member 82 of syringe actuation handle 80, such as that shown in FIG. 8. Member 82 of syringe actuation handle 80 is pivotally associated with another member 84 of syringe actuation handle 80, with member 84 being coupled to a syringe plunger 86. Nonlimiting examples of such syringe actuation handles are described in U.S. Pat. No. 7,534,234, issued May 19, 2009, and U.S. Pat. No. 7,674,247, issued Mar. 9, 2010.

As noted previously, in some embodiments, rotatable element 40", 40''' may be disassembled from a barrel 20 (or any other embodiment of barrel, such as barrel 20' or barrel 120) (see, e.g., the embodiment of rotatable element 40 shown in FIGS. 1 through 3). In such embodiments, once a barrel 20 has been used, it may be removed from rotatable element 40", 40''', disposed of, and replaced with a different barrel 20a. Thus, the handles (e.g., handle 62 (FIG. 6) or handle 80 (FIG. 8)) that are associated with such a rotatable element 40", 40''' may be reused, which may reduce the expenses that have conventionally been incurred when many types of syringes, including, but not limited to, control and leveraged syringes, are used.

Figure 9:
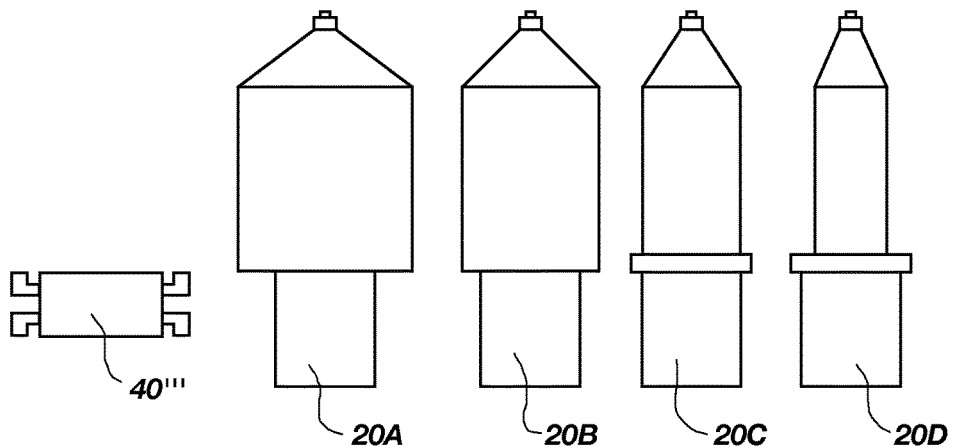
FIG. 9 schematically illustrates a system including a variety of different barrel configurations and a rotatable element that are configured for use with various embodiments of handles.

By enabling barrel replacement, the use of a rotatable element of the present invention (e.g., rotatable element 40", 40''', etc.) in conjunction with reusable handles (e.g., handles 62, 80, etc.) provide a modular system that may be used with syringe barrels 20A, 20B, 20C, 20D (which may, e.g., be configured as barrel 20, 20', 120 etc.) of a variety of different configurations, as shown in FIG. 9. By way of example only, barrels of a plurality of different volumes, of a plurality of different dimensions, that include a plurality of different optional features (e.g., no optional features, release valves, ports configured for connection to pressure gauges and other apparatus, inlet ports, etc.), or the like may be used with one reusable handle. Of course, differently configured syringe barrels that are configured for use with the same rotatable element may have commonly-dimensioned features for engagement by the rotatable element, or may be used in combination with adapters that facilitate their use with the same rotatable element.

Figure 10:
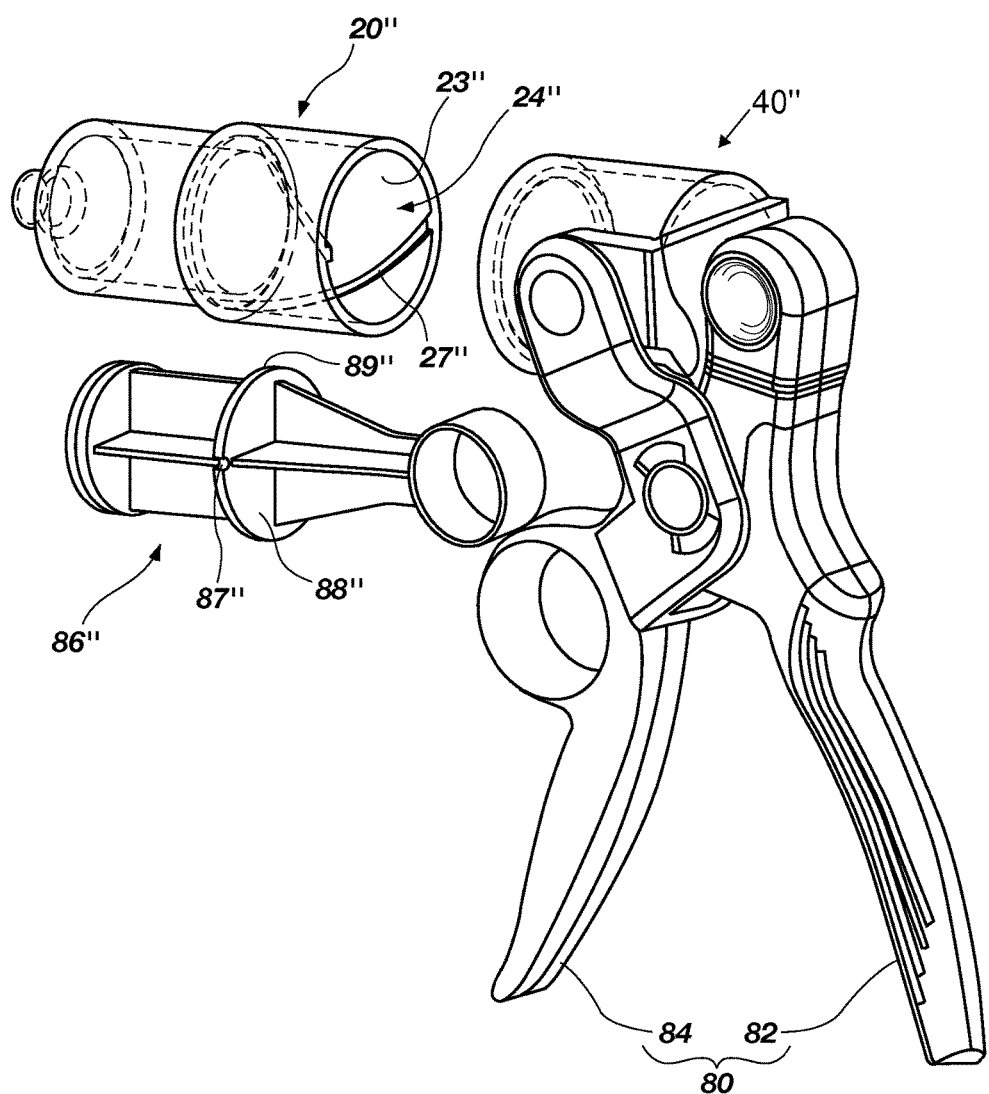
FIG. 10 is a perspective representation of an embodiment of a syringe of the present invention in which a barrel of the syringe rotates as a plunger of the syringe moves along a length of the barrel.

As shown in FIG. 10, a rotatable element 40" that incorporates teachings of the present invention is particularly useful with embodiments of barrels 20" that are configured to rotate as their corresponding plungers 86" are drawn therefrom. Such barrels 20" and their corresponding plungers 86" may include cooperating rotation elements that cause barrel 20" to rotate as plunger 86" is moved axially along (i.e., forced into or withdrawn from) a receptacle 24"of barrel 20".

In a specific embodiment, an interior surface 23" of such a barrel 20" carries one or more threads 27" (two threads 27" are shown in the illustrated embodiment). Threads 27" are elongate, curved elements that are at least partially helically oriented and configured to engage or to be engaged by cooperating features of plunger 86" and to cause rotational movement of barrel 20" relative to plunger 86". In a more specific embodiment, threads 27" protrude from interior surface 23" into receptacle 24".

An embodiment of plunger 86" that corresponds to barrel 20" may include an engagement feature 87", such as the depicted notch, that receives and cooperates with a corresponding thread 27". In a more specific embodiment, each engagement feature 87" is formed in an alignment element 88" of plunger 86". Even more specifically, each engagement feature 87" may be formed in an edge 89" of alignment element 88" (illustrated as an alignment disk) of plunger 86". As shown, alignment element 88" may be located at a proximal end of plunger 86" (i.e., the end that will be located closest to an individual operating a syringe that includes barrel 20" and plunger 86"). Edge 89" of alignment element 88" abuts against interior surface 23" of barrel 20" to align plunger 86" with receptacle 24" of barrel 20" as plunger 86" is forced through receptacle 24", along the length of barrel 20". As plunger 86" is inserted into receptacle 24" of barrel 20" and is driven axially along the length of barrel 20", each engagement feature 87" continues to engage its corresponding thread 27". Due to the helical orientation of threads 27", movement of plunger 86" along the length of barrel 20" causes barrel 20" to rotate relative to plunger 86", as plunger 86" is forced through (i.e., into or out of) receptacle 24". In the depicted embodiment, movement of plunger 86" out of receptacle 24" (i.e., proximally, toward an individual using a syringe including barrel 20" and plunger 86") is effected as members 82 and 84 of syringe actuation handle 80 are forced together.

Embodiments of syringes with rotatable elements 40" and barrels 20" that rotate relative to their plungers 86" may be used in a variety of procedures, including, but not limited to, processes in which samples (e.g., biological samples, samples from the body of a subject, etc.) are obtained.

In a biopsy embodiment, a biopsy needle may be rigidly secured to barrel 20". Movement of plunger 86" along the length of barrel 20" may cause barrel 20" and the biopsy needle to rotate about axes extending along their lengths, enabling use of the biopsy needle in a coring and aspiration technique to manually obtain a sample. A hand held syringe incorporating teachings of the present invention may be advanced and operated manually, even with a single hand, which may free the operator's other hand for a variety of purposes, including, without limitation, stabilization of a patient, control of an imaging device, such as an ultrasound apparatus, or the like.

In embodiments where a catheter is rigidly coupled to a barrel 20" that rotates as its corresponding plunger 86" is driven along its length, actuation of plunger 86" may rotate the catheter about an axis extending along its length, which may be useful in breaking up or dislodging obstructions, removing blood clots or thrombi, or in mixing fluids prior to or during their aspiration.

Figure 11:
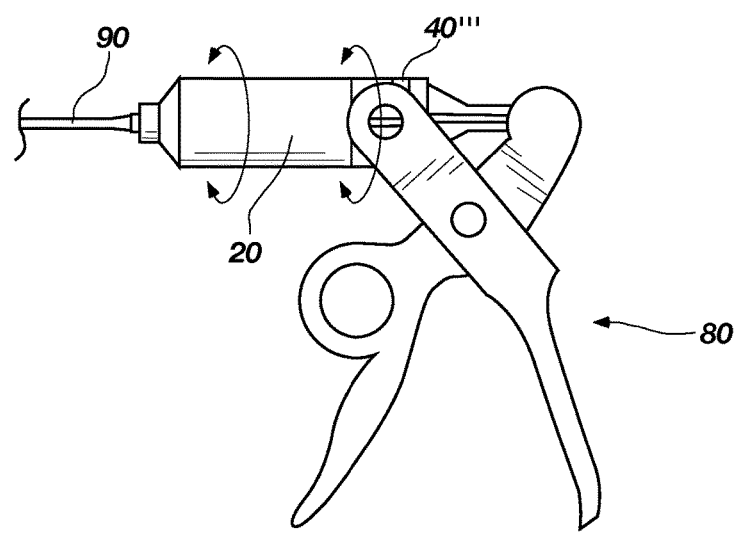
FIG. 11 is a schematic view of a system including a syringe with a rotatable element around a syringe barrel and an aspiration element secured to a distal end of the syringe barrel.

Referring now to FIG. 11, in use, a rotatable element that incorporates teachings of the present invention (e.g., rotatable element 40, 40', 40", etc.) allows for some movement of syringe handles (e.g., handle 62, syringe actuation handle 80, etc.) while the barrel (e.g., barrel 20, 20', etc.) and a distally located peripheral device 90, such as a catheter or needle, remains substantially stationary. Thus, a syringe according to the present invention eliminates the need for relatively complex and expensive rotatable fittings, or coupling elements, such as slip ring luer locks.

In addition to being able to rotate about a barrel (e.g., barrel 20 or 20'), such as during rotational movement of a handle or handles (e.g., handle 62, syringe actuation handles 80, etc.) relative to the barrel, a rotatable element (e.g., rotatable element 40, 40", 40''', etc.) that embodies teachings of the present invention enables the barrel to rotate as the rotatable element and any handles associated with the rotatable element are held (e.g., by a handle 62, 80, etc.) in a stationary or somewhat stationary (accounting for normal movement by a healthcare provider operating the handle) position. This feature may be useful for coupling a syringe of the present invention to a distally located peripheral device 90 that is already in place in a subject's body.

Although the foregoing description contains many specifics, these should not be construed as limiting the scope of the present invention, but merely as providing illustrations of some of the presently preferred embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions and modifications to the invention as disclosed herein which fall within the meaning and scope of the claims are to be embraced thereby.

What is claimed:

1. A method for using a syringe comprising:
securing a device to a barrel of the syringe;
grasping a handle associated with a rotatable element on the barrel; and
actuating the handle to:
force a plunger longitudinally through the barrel; and
cause the barrel to rotate about a longitudinal axis of the barrel and the device to rotate about the longitudinal axis of the barrel while the handle is held in a substantially stationary rotational position relative to the longitudinal axis of the barrel.

2. The method of claim 1, wherein:
securing the device to the barrel comprises securing a biopsy needle to the barrel; and
actuating the handle facilitates:
coring of a sample with the biopsy needle; and
aspirating the sample into at least the biopsy needle.

3. The method of claim 1, wherein:
securing the device to the barrel comprises securing a catheter to the barrel; and
actuating the handle causes:
rotation of the catheter about an axis extending along a length of the catheter; and
aspirating a sample into the barrel.

4. The method of claim 1, wherein actuating the handle comprises drawing the plunger proximally through the barrel.

5. The method of claim 4, wherein actuating the handle comprises forcing aspiration handles together.

6. The method of claim 1, wherein actuating the handle comprises forcing the plunger distally through the barrel.

7. The method of claim 6, wherein actuating the handle comprises forcing injection handles together.

* * * * *